United States Patent [19]

Bernardini

[11] Patent Number: 4,782,835
[45] Date of Patent: Nov. 8, 1988

[54] REFILL UNIT FOR PORTABLE HEAT TREATMENT SYSTEM

[75] Inventor: Ronald J. Bernardini, Ambler, Pa.

[73] Assignee: Michael Litman, Huntingdon Valley, Pa. ; a part interest

[21] Appl. No.: 31,345

[22] Filed: Mar. 26, 1987

Related U.S. Application Data

[62] Division of Ser. No. 376,000, May 7, 1982, Pat. No. 4,696,303.

[51] Int. Cl.4 .............................................. A61F 7/00
[52] U.S. Cl. .................................................. 128/403
[58] Field of Search ............... 128/369, 370, 399, 402, 128/403, 365; 604/113, 290, 291; 220/3.1, 412; 126/343.5 A; 219/207

[56] References Cited

U.S. PATENT DOCUMENTS

| | | | |
|---|---|---|---|
| 527,057 | 10/1894 | Goldman | 128/369 |
| 1,863,533 | 6/1932 | Odell | 128/370 |
| 2,396,578 | 3/1946 | Kittel et al. | 126/343.5 A |
| 2,463,329 | 3/1949 | Stansbury | 219/207 |
| 2,904,037 | 9/1959 | Cassidy | 128/370 |
| 3,157,774 | 11/1964 | Moore et al. | 128/370 |
| 3,244,210 | 4/1966 | Clarizio | 128/402 |
| 4,149,536 | 4/1979 | Villard | 128/365 |

Primary Examiner—Max Hindenburg
Attorney, Agent, or Firm—Caesar, Rivise, Bernstein, Cohen & Pokotilow

[57] ABSTRACT

A portable heat treatment system in accordance with this invention includes a heating shoe having a heat conductive base member and heating means for transmitting heat along the base member. A heat conductive container having a base with peripheral walls extending upwardly therefrom defines a heat treating compartment, and the container is removably retained within the heating shoe with the base of the container being supported by the heat conductive base member of the shoe. A packaged, heat conductive container of body-treating material also constitutes part of this invention.

2 Claims, 2 Drawing Sheets

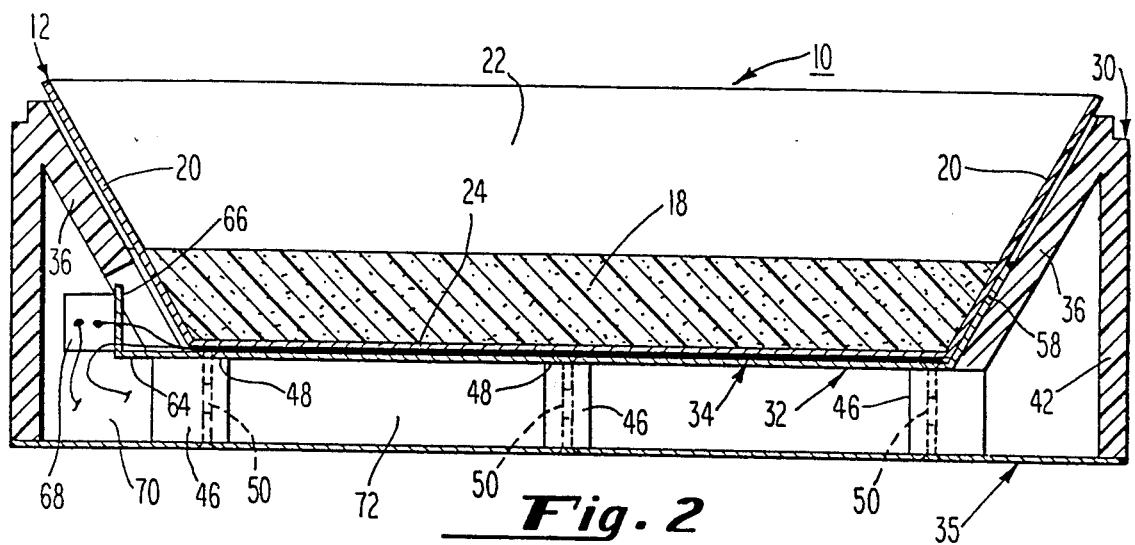
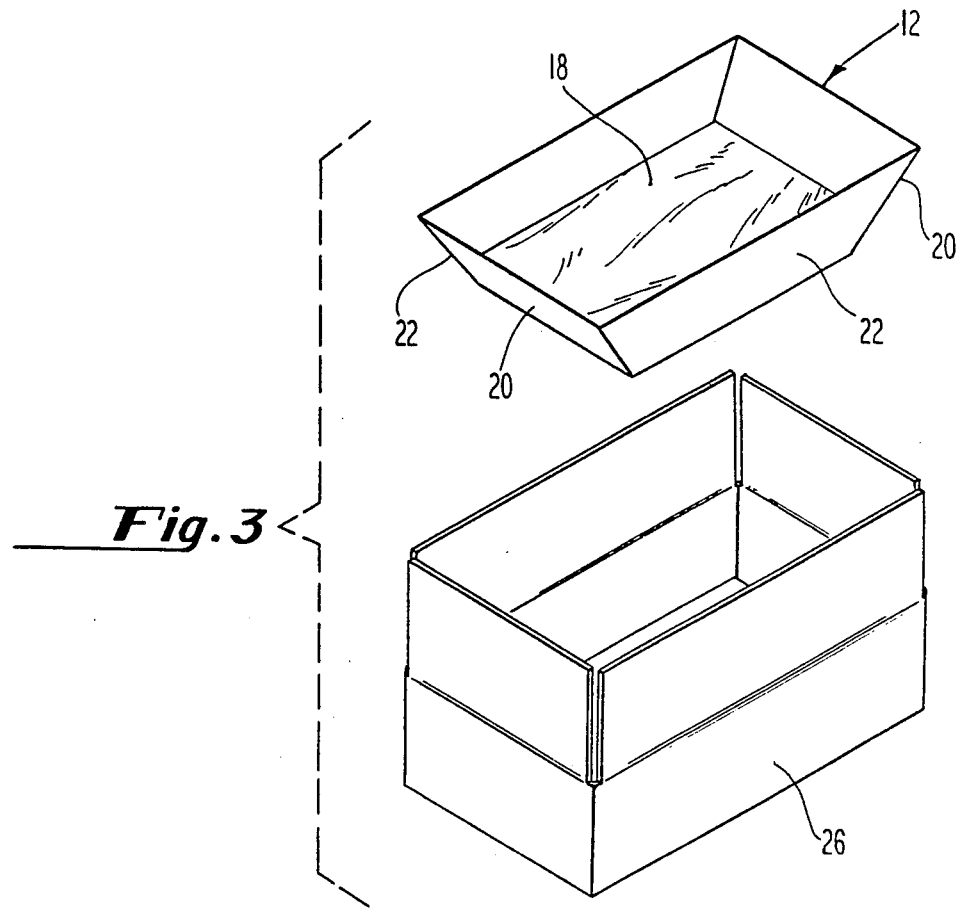

REFILL UNIT FOR PORTABLE HEAT TREATMENT SYSTEM

RELATED APPLICATION

This is a divisional application of U.S. application Ser. No. 376,000, filed May 7, 1982, now U.S. Pat. No. 4,696,303, issued on Sept. 29, 1987.

FIELD OF INVENTION

This invention relates generally to a portable heat treatment system, and more specifically to a system that is well suited for the treatment of parts of the human body with a paraffin-type wax or similar treatment material.

BACKGROUND ART

Portable paraffin baths for administering heat therapy to parts of the human body are well known. One such device which has been in commercial use for a considerable period of time is sold under the trademark THERABATH. This unit includes a tank in which the paraffin wax is retained. When the bath is being employed daily in home use, it is desirable to replace the wax approximately once a month, and then to thoroughly clean the tank. When the unit is being used in a clinic or other physical therapy department, it is recommended that the wax applied to the patients body be disgarded after each application.

In order to remove the wax from the prior art system, referred to above, it is recommended that the wax first be cooled to permit it to solidify. Then, to remove the solid block, it is necessary to slightly re-heat the wax to thereby loosen it from the tank walls. Any wax that still remains on the walls is blotted out with paper towels, and if necessary, the bath is again heated to loosen any remaining solidified wax. After removal of all of the wax, it is recommended by the manufacturer that a soapy cloth first be used to clean the tank, and that a dry cloth then be used to complete the cleaning operation.

From the above explanation, it should be apparent that the cleaning operation is somewhat cumbersome In fact, if the individual attempting to clean the tank is the one being treated for an affliction such as arthritis or bursitis of the hands, the cleaning operation itself can provide a very painful experience.

It should also be pointed out that the above-discussed prior art tank weighs approximately 6 to 8 pounds, without the block of paraffin in it. With approximately 3 pounds of paraffin the unit weighs between 9 to 11 pounds. In either event the portability of the unit would be enhanced if its weight were reduced.

U.S. Pat. No. 3,157,774, issued to Moore et al, discloses a portable paraffin bath wherein the paraffin is retained in an inner container and indirectly heated by a heat exchange liquid, such as water. The bath disclosed in Moore is somewhat complex; including two drainage systems; one for removing the treatment material (e.g. paraffin), and the other for removing the heat exchange liquid (e.g. water). Moreover, once the treatment liquid has been removed from the inner container, a manual cleaning operation, similar to that required in connection with the Therabath system, needs to be employed.

U.S. Pat. No. 4,149,536, issued to Villard, although relating to a paraffin wax treatment system, employs a spray gun for applying the treatment fluid to the part of the body requiring treatment. This is significantly different from, and employs an entirely different structural arrangement of elements than the present invention.

U.S. Pat. No. 2,463,329, issued to Stansbury, also discloses a therapeutic bath employing paraffin In this construction the metal vessel 20 in which the paraffin is retained is a fixed part of the unit, i.e. it is not removable from its supporting structure. In fact, the invention disclosed in this patent is directed predominately to the paraffin drainage system associated with the vessel.

U.S. Pat. No. 2,396,578, issued to Kittel et al, is referenced herein because it does relate generally to an apparatus for heating and melting plastic or similar material. This apparatus employs an indirect heating system similar to that employed in the apparatus disclosed in the earlier-discussed Moore et al U.S. Pat. No. (3,157,774), but does not relate to a heat therapy system of the type designed to accommodate part of the human body.

The invention described hereinafter is particularly well suited for heat therapy applications.

DISCLOSURE OF INVENTION

This invention relates to a light-weight, portable heat treatment system; particularly well suited for administering heat therapy to parts of the human body for such ailments as arthritis, bursitis and chronic joint inflammation. In particular, the system is most desirably employed with paraffin-type wax to carry out the therapeutic treatment.

A portable heat treatment system in accordance with this invention includes a heating shoe, said shoe having a heat conductive base member and heating means for transmitting heat along said base member; a heat conductive container having a base with peripheral walls extending upwardly therefrom for defining a heat treating compartment; said container being removably retained within the heating shoe with the base of said container being supported by the heat conductive base member of said shoe.

As indicated above, in the most preferred embodiment of this invention the heat treating compartment includes a paraffin-type wax material for providing treatment to a part of the human body. Most preferably the container is removably retained in the heating shoe solely by its own weight (e.g. by gravity), whereby it can be removed easily merely by lifting it out of the supporting shoe.

In accordance with this invention the container, with paraffin wax retained therein, is packaged and sold as a separate item. Therefore, when it is desired to change the wax, a replacement package is merely substituted for the spent package. This completely eliminates the need for emptying the wax-containing compartment and thereafter cleaning it; a significant improvement over the prior art constructions that require draining and cleaning of the compartment prior to introducing the fresh charge of wax.

In accordance with the preferred embodiment of this invention the main body of the heating shoe is a unitary, light-weight, injection molded part which is extremely easy and economical to fabricate. In fact, the entire weight of the system, including the container with paraffin in it, will be less than 6 pounds; preferably in the range of 4 to 5 pounds.

In the most preferred embodiment of this invention the heating means employed in connection with the heat conductive base member of the shoe is a flexible foil heater of a well known construction, and this heater is secured adhesively to the heat conductive base member. In this arrangement the base of the heat conductive, paraffin-retaining container is directly supported on the flexible foil heater to carry out the heating operation.

The heat conductive base member preferably is constructed of aluminum, or similar high heat conducting material. Most preferably the base member includes peripheral end walls and sidewalls which closely conform to the peripheral walls of the heat-conductive container for efficiently transmitting heat through the peripheral container walls to melt the paraffin wax. Most preferably the height of the peripheral walls of the heat conductive base member is at least approximately equal to the depth to which the heat conductive container is filled with the solid paraffin wax. This provides for extremely effective heat transfer to the wax-retaining area of the container for melting the wax preparatory to carrying out the therapeutic heat treating operation.

Other objects and a fuller understanding of the invention will be had by referring to the following description of the Best Mode of the Invention, taken in conjunction with the accompanying drawings.

BRIEF DESCRIPTION OF THE DRAWINGS

FIG. 2 is a cross-sectional view of the system illustrated in FIG. 1, but with the parts assembled, except for the lid; and FIG. 3 is an exploded isometric view of the package of treating material in accordance with a further aspect of this invention.

BEST MODE OF THE INVENTION

Figure 1:
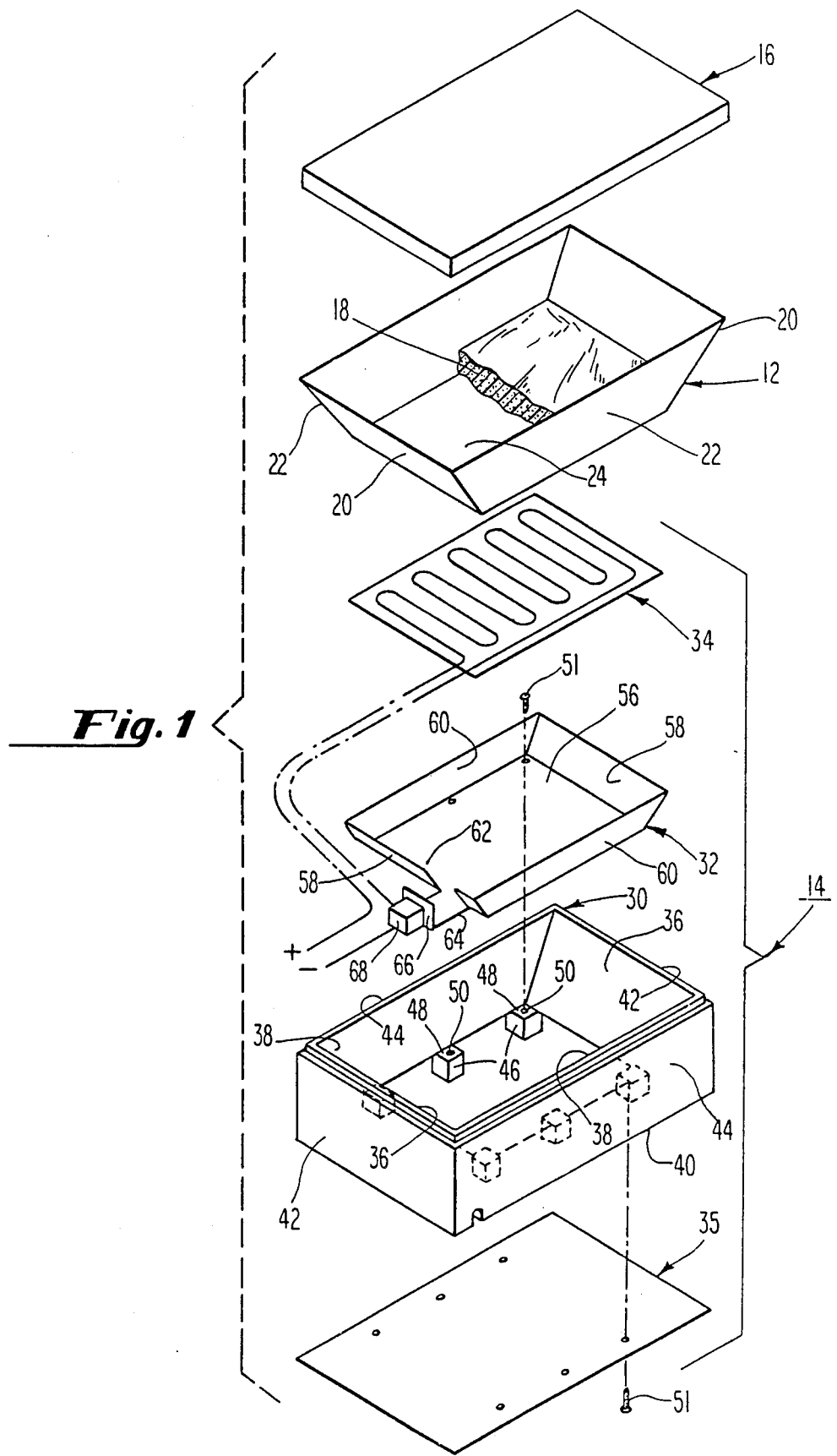
FIG. 1 is an exploded isometric view of a preferred embodiment of the heat treatment system of this invention.

Referring to FIGS. 1 and 2, the heat treatment system 10 in accordance with this invention includes a heat conductive container 12 removably retained within a heating support member 14, also referred to herein as a heating shoe. In fact, the heat conductive container 12 actually is supported in the shoe 14 solely by its own weight (i.e., by gravity), and can be removed easily by merely lifting it out of the shoe. The construction of the system 10 is completed by a top, or cap 16 employed to close the open end of the container 12 for preventing contamination of the system when it is not in use.

Referring to FIGS. 1 and 3, the heat conductive container 12, preferably tin-plated or formed from a similar heat conductive material, includes a charge of paraffin wax 18. Preferably the paraffin wax includes a skin conditioner, such as lanolin or glycerin, and is compounded to melt at a temperature of approximately 120° F. The container 12 includes sloping end walls 20 and sloping sidewalls 22; diverging outwardly from a flat bottom wall 24.

Referring specifically to FIG. 3, the container 12, in accordance with the present invention, is packaged for sale as a separate replacement unit for use in conjunction with the heating shoe 14. In fact, it can be packaged in many different ways; one preferred way being to retain it within a conventional box 26.

Referring to FIGS. 1 and 2, the heating shoe 14 includes a unitary injection molded housing 30, a conductive heater plate or base member 32, a flexible foil heater 34 and a bottom closure plate 35.

In a preferred construction of this invention the housing 30 is injection molded from a glass-filled plastic, such as Nylon 6—6 having a melting point of about 485° F. It is important that the plastic utilized to form the housing have a sufficiently high melting point to prevent it from distorting or melting when it is employed to heat the paraffin wax to its melting point (e.g. approximately 120° F). It should be understood that other suitable materials can be employed to form the housing 30 provided they have the required heat stable characteristics.

The injection molded housing 30 includes inner peripheral end walls 36 and inner peripheral sidewalls 38, all of which terminate short of lower surfaces, or margins 40 of the outer peripheral end walls 42 and sidewalls of said housing. A plurality of bosses 46, preferably six in number, are molded as continuous extensions of the inner peripheral walls 36 and 38. Most preferably a boss is provided at each of the four junctions between the end walls and sidewalls, and two additional bosses are provided at the midpoint of each of the sidewalls. These six bosses are spaced from each other and include upper flat surfaces 48 substantially in a common horizontal plane for supporting the conductive heater plate 32; preferably formed of aluminum or other highly heat conductive material. Each of the bosses 46 is provided with a screw-receiving passage 50 extending completely through its length. Screws (e.g. 51) cooperate with each of the bosses to firmly secure the conductive heater plate 32 and the bottom closure plate 35 to the injection molded housing 30. When the heater plate 32 is fastened to the bosses 46, it cooperates with the inner peripheral walls 36 and 38 of the housing to define a frusto-conical compartment that closely conforms to the frustro-conical configuration of the heat conductive container 12. In fact, the sloping end walls 20 and sloping sidewalls 22 of the container 12 match the slope of the inner peripheral end walls 36 and sidewalls 38 of the housing 30, and the bottom wall 24 of the container 12 is only slightly smaller in width and length than a flat lower wall 56 of the heater plate 32 (FIG. 1).

Referring to FIGS. 1 and 2, the heater plate 32, in addition to having a flat lower wall 56, includes sloping peripheral end walls 58 and sloping peripheral sidewalls 60. One of the end walls 58 is interrupted at 62, and a tongue 64, constituting a continuous extension of the flat lower wall 56, projects outwardly beyond the end wall 58, and terminates in an upwardly directed section 66. A thermostat 68 is secured to the upright section 66 of the heat conductive plate 32 to control the temperature of the paraffin wax 18. Many different types of thermostats can be employed in this invention; one preferred type being a conventional bimetallic adjustable appliance thermostat that is preset at the factory to control the operation of the flexible foil heater 34 for maintaining the paraffin wax at the desired temperature. It should be understood that a variable thermostat also could be used in connection with this invention.

The flexible foil heater 34 is of a conventional design; one acceptable heater being sold by Ohmweve Co., and being rated at 147 ohms, 0.8 amps at 96 watts. This foil heater 34 preferably is attached by adhesive (not shown) to the lower wall 56 of the conductive heater 32. Due to the high heat conductivity of the plate 32, the heat from the flexible foil heater will be transmitted evenly over the entire plate, including the section 66, to thereby control the operation of the thermostat 68. Note that the sloping end walls 58 and sloping sidewalls 60 of the heater plate 32 are positioned closely adjacent corresponding sloping end walls and sidewalls 20 ad 22, respectively, of the container 12. In fact, the sloping end walls and sidewalls of the heater plate 32 extend up the peripheral walls of the container 12 a distance substantially equal to the depth of the solid paraffin wax retained within said container (FIG. 2). In an exemplary embodiment of this invention about three pounds of paraffin wax is retained in a tin-plated pan dimensioned to establish a paraffin wax depth of about 1½ inches.

Referring specifically to FIG. 2, the thermostat 68 is located within a peripheral chamber 70 formed between the inner and outer peripheral walls of the injection molded housing 30 and extending completely around the periphery of said housing. This chamber 70 communicates, between the spaced-apart bosses 46, with a lower compartment 72, located beneath the conductive heater plate 32. Before the bottom plate 35 is secured to the injection molded housing 30 to close off the chamber 70 and compartment 72, a conventional plug (not shown) is electrically connected to the leads of the foil heater through the thermostat 68 in a well-known conventional manner. To this end the leads 76 of the foil heater are directed through the interruption 62 in the end wall 58 of the heater plate 32 so that the necessary connections of these leads to the thermostat 68 and plug can be made.

From the above description it should be apparent that this invention embodies several significant advantages over the prior art. The injection molded housing 30 aids in establishing an extremely light-weight portable structure. The structural arrangement between the flexible foil heater 34 and the conductive heater plate 32 provides excellent control over the heating operations to both melt the paraffin wax retained within the container 12, and also to maintain the wax at the desired treatment temperature. The unique manner of removably mounting the container 12 within the heat shoe 14 also constitutes a distinct advantage over prior art structures. Moreover, the individual packaging of replacement packages eliminates time-consuming and burdensome cleaning operations required with other systems.

Although I have described the present invention with reference to the particular embodiment of the invention herein set forth, it is understood that the present disclosure has been made only by way of example and that numerous changes in the details of construction may be resorted to without departing from the spirit and scope of the invention. Thus, the scope of the invention should not be limited to the foregoing specification, but rather to the scope of the claims appended hereto.

I claim:

1. A replacement refill unit usable in conjunction with a heating shoe of a portable heat treatment system to administer heat treatment to a part of the human body characterized in that said unit includes a heat conductive container having an inner surface defining a compartment, a body treating wax material which is solid at room temperature, said solid body treating wax material only partially filling the compartment and being adapted to be melted by use of the heating shoe, and packaging means for said partially filled container.

2. The replacement refill unit of claim 1 characterized in that the solid body treating wax material is in close conformity with the inner surface defining the compartment of the heat conductive container.

* * * * *